United States Patent [19]

Miller

[11] Patent Number: 5,244,805
[45] Date of Patent: Sep. 14, 1993

[54] BACULOVIRUS EXPRESSION VECTORS

[75] Inventor: Lois K. Miller, Athens, Ga.

[73] Assignee: University of Georgia Research Foundation, Inc., Athens, Ga.

[21] Appl. No.: 635,561

[22] Filed: Jan. 17, 1991

Related U.S. Application Data

[63] Continuation-in-part of Ser. No. 353,847, May 17, 1989, abandoned.

[51] Int. Cl.$^5$ .............................................. C12N 15/86
[52] U.S. Cl. .............................. 435/320.1; 435/69.1; 435/91.41; 435/172.3; 536/24.1
[58] Field of Search ...................... 435/91, 69.1, 172.3, 435/320.1, 70.1

[56] References Cited

U.S. PATENT DOCUMENTS 4,745,051 5/1983 Smith et al. ........................ 435/69.1

FOREIGN PATENT DOCUMENTS 3529189 7/1989 Australia.
0155476 9/1985 European Pat. Off..
9010078 9/1990 PCT Int'l Appl..

OTHER PUBLICATIONS

DeBoer et al. PNAS, vol. 80, pp. 21-25, 1983.
Takehara et al. J. Gen. Virol. vol. 69, pp. 2763-2777, 1988.
Friesen et al. J. of Virol., vol. 61, pp. 2264-2272, 1987.
McKnight et al., Science, vol. 217, pp. 316-324, 1982.
Miyamoto et al., Mol. Cell. Biol., vol. 5 pp. 2860-2865, 1985.
Rankin et al. (1988) Gene 70:39-49.
Luckow et al. (1987) BioTechnology 6:47-55.
Miller et al. (1986) Genetic Engineering: Principles and Methods pp. 277-298.
Miller. (1988) Ann. Rev. Microbiol. 42:177-199.
Matsuura et al. (1987) J. Gen. Virol. 68:1233-1250.
Wilson et al. (1987) J. Virol. 61:661-666.
Ooi et al. (1989) J. Mol. Biol. 210:721-736.
Rohrmann (1986) J. Gen. Virol. 67:1499-1513.
Luckow et al. (1988) Virol. 167:56-71.
Vlak et al. (1988) J. Gen. Virol. 69:765-776.
Friesen et al. (1986) Curr. Topics Microbiol. Immunol. 131:31-49.
Iatrou et al. (1989) Gene 75:59-71.
Horiuchi et al. (1987) Agric. Biol. Chem. 51:1573-1580.

Primary Examiner—Richard A. Schwartz
Assistant Examiner—David Guzo
Attorney, Agent, or Firm—Greenlee and Winner

[57] ABSTRACT

A method and composition for improving the level of expression of a gene or collection of genes by providing a novel baculovirus promoter to which a heterologous gene is attached. The novel promoter may contain a modification of a natural viral promoter or may be totally synthetic. The novel baculovirus promoter may also comprise a combination promoter such as a promoter with a double start site or a combination of two different promoters. Foreign gene placement in a novel location or genomic orientation is also included.

14 Claims, 7 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 187 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
GATATCATGG AGATAATTAA AATGATAACC ATCTCGCAAA TAAATAAGTA TTTTACTGTT      60

TTCGTAACAG TTTTGTAATA AAAAACCTA TAAATAGATC TCGACGAGAT TTTCAGGAGC      120

TAAGGAAGCT AAAATGGAGA AAAAATCAC TGGATATACC ACCGTTGATA TATCCCAATG      180

GCATCGT                                                                187
```

( 2 ) INFORMATION FOR SEQ ID NO:2:

( i ) SEQUENCE CHARACTERISTICS:
( A ) LENGTH: 97 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:2:

GATATCATGG AGATAATTAA AATGATAACC ATCTCGCAAA TAAATAAGTA TTTTACTGTT        60

TTCGTAACAG TTTTGTAATA AAAAAACCTA TAAATAG                                97

( 2 ) INFORMATION FOR SEQ ID NO:3:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

GATATCATGG AGCCAAGCTT GGTGATAACC ATCTCGCAAA TAAATAAGTA TTTTACTGTT        60

TTCGTAACAG TTTTGTAATA AAAAAACCTA TAAATAG                                97

( 2 ) INFORMATION FOR SEQ ID NO:4:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

GATATCATGG AGATAATTAA AACCAAGCTT GGCTCGCAAA TAAATAAGTA TTTTACTGTT        60

TTCGTAACAG TTTTGTAATA AAAAAACCTA TAAATAG                                97

( 2 ) INFORMATION FOR SEQ ID NO:5:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

GATATCATGG AGATAATTAA AATGCCAAGC TTGGCGCAAA TAAATAAGTA TTTTACTGTT        60

TTCGTAACAG TTTTGTAATA AAAAAACCTA TAAATAG                                97

( 2 ) INFORMATION FOR SEQ ID NO:6:

( i ) SEQUENCE CHARACTERISTICS:
        ( A ) LENGTH: 95 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

GTACCTCCCG GGCCAAGCTT GGCGTTATTG AATAAGAATT TAAAAATCAA TCATTTGTAT        60

ACTGTAAATT ACATACTGTT TTATTTAACA ATAGA                                  95

( 2 ) INFORMATION FOR SEQ ID NO:7:

( i ) SEQUENCE CHARACTERISTICS:
        ( A ) LENGTH: 162 base pairs
        ( B ) TYPE: nucleic acid
        ( C ) STRANDEDNESS: double
        ( D ) TOPOLOGY: linear (i i) MOLECULE TYPE: DNA (genomic)

(i x) FEATURE:
    (A) NAME/KEY: miscfeature
    (B) LOCATION: 92..160
    (D) OTHER INFORMATION: /note="mcs #Microsoft Corp (x i) SEQUENCE DESCRIPTION: SEQ ID NO:7:

| | | | | | | |
|---|---|---|---|---|---|---|
| GATGTCCCGG | GCCAAGCTTG | GCGTTATTGA | ATAAGAATTT | AAAAATCAAT | CATTTGTATA | 60 |
| CTGTAAATTA | CATACTGTTT | TATTTAACAA | TAGATATCGA | ATTCCTGCAG | CCGGGGATC | 120 |
| CACTAGTTCT | AGAGCGGCCG | CCACCGCGGT | GGAGCTCCAA | TC | | 162 |

(2) INFORMATION FOR SEQ ID NO:8:

(i) SEQUENCE CHARACTERISTICS:
        (A) LENGTH: 473 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:8:

| | | | | | | |
|---|---|---|---|---|---|---|
| GATATCTTGT | TCGCCATCGT | GGAATCAAAT | AGATCAATGT | CACTTTTCGA | AAAATATACA | 60 |
| TGTTCAAATT | TGATTTCAAT | TTTATCGTGT | TGGTAAACGT | ACACTTAAT | TATTTTACTC | 120 |
| AAGTTGTGCG | AAAGAGTCTT | GTAAGGCAGT | TTGATTTCTT | TGCTTTCTCT | CCACACCAAC | 180 |
| GGCACCAACG | CGTTGGTATC | TTTAGGCCAA | TAAACAATT | TTTTGTGTTT | GGAATTAGTC | 240 |
| TTTTTCACGC | TTGATATTAT | GTTATTGCAA | GCGCTCTGAA | TAGGTATACG | AGTGCGAAAG | 300 |
| CCGTTTTCGT | CGTACAAATC | GAAATATTGT | TTGCCAGCGA | ATAATTAGGA | ACAATATAAG | 360 |
| AATTTAAAAT | TTTATACAAC | AAATCTTGGC | TAAAATTTAT | TGAATAAGAG | ATTTCTTTCT | 420 |
| CAATCACAAA | ATCGCCGTAG | TCCATATTTA | TAACGGCAAC | AATATGCAGA | TCT | 473 |

(2) INFORMATION FOR SEQ ID NO:9:

(i) SEQUENCE CHARACTERISTICS:
        (A) LENGTH: 448 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:9:

| | | | | | | |
|---|---|---|---|---|---|---|
| GATATCTTGT | TCGCCATCGT | GGAATCAAAT | AGATCAATGT | CACTTTTCGA | AAAATATACA | 60 |
| TGTTCAAATT | TGATTTCAAT | TTTATCGTGT | TGGTAAACGT | ACACTTAAT | TATTTTACTC | 120 |
| AAGTTGTGCG | AAAGAGTCTT | GTAAGGCAGT | TTGATTTCTT | TGCTTTCTCT | CCACACCAAC | 180 |
| GGCACCAACG | CGTTGGTATC | TTTAGGCCAA | TAAACAATT | TTTTGTGTTT | GGAATTAGTC | 240 |
| TTTTTCACGC | TTGATATTAT | GTTATTGCAA | GCGCTCTGAA | TAGGTATACG | AGTGCGAAAG | 300 |
| CCGTTTTCGT | CGTACAAATC | GAAATATTGT | TTGCCAGCGA | ATAATTAGGA | ACAATATAAG | 360 |
| AATTTAAAAT | TTTCCAAGCT | TGCGCAAATA | AATAAGTATT | TTACTGTTTT | CGTAACAGTT | 420 |
| TTGTAATAAA | AAAACCTATA | AATAGATC | | | | 448 |

BACULOVIRUS EXPRESSION VECTORS

The United States government may have certain rights in this invention. This work was funded by grant No. AI23719 from the National Institutes of Health.

This application is a continuation-in-part of U.S. patent application Ser. No. 07/353,847, filed May 17, 1989, now abandoned.

TECHNICAL FIELD

The present invention relates to methods and compositions for improving the expression of a gene. More particularly, the present invention relates to classes of novel promoters that improve the expression of a heterologous gene in a baculovirus system.

BACKGROUND OF THE INVENTION

As used throughout this specification, the following definitions apply for purposes of the present invention:

The term "expression" may be characterized in the following manner. A cell is capable of synthesizing many proteins. At any given time, many proteins which the cell is capable of synthesizing are not being synthesized. When a particular polypeptide, coded for by a given gene, is being synthesized by the cell, that gene is said to be expressed. In order to be expressed, the DNA sequence coding for that particular polypeptide must be properly located with respect to the control region of the gene. The function of the control region is to permit the expression of the gene under its control.

The term "vector" refers to an extra-chromosomal molecule of duplex DNA comprising an intact replicon that can be replicated in a cell. Generally, vectors are derived from viruses or plasmids of bacteria and yeasts. A baculovirus vector comprises a baculovirus replicon.

The term "gene" refers to those DNA sequences which transmit the information for and direct the synthesis of a single protein chain.

The term "infection" refers to the invasion by agents (e.g., viruses, bacteria, etc.) of cells where conditions are favorable for their replication and growth.

The term "transfection" refers to a technique for infecting cells with purified nucleic acids of viruses.

The term "heterologous gene" in reference to the baculovirus vectors hereof, refers to DNA that encodes polypeptides ordinarily not produced by the virus from which the vector is derived, but which is introduced into the cell as recombinant DNA or within viruses carrying recombinant DNA genomes. The terms "passenger gene" or "passenger DNA" as used herein are equivalent to the term "heterologous gene." "Exogenous," as used herein, has the same meaning as heterologous.

The term "transplacement plasmid" means a bacterial vector which is used as an intermediate in the construction of a virus vector. A transplacement plasmid facilitates the transfer of exogenous genetic information, such as the combination of a novel promoter and a heterologous structural gene under the regulatory control of that promoter, to a specific site within the viral genome by homologous recombination. That homologous recombination occurs via the DNA sequences flanking the chimeric gene.

The science of genetic engineering has advanced to a stage wherein certain biologically useful products can be produced in large quantities. For example, two commercially successful drugs, human growth hormone and tissue plasminogen activator (t-PA), are now being produced in large quantities and are being used to treat a variety of pathological conditions. However, scientists are constantly trying to discover new and more efficient systems for producing the proteins and other products in various biological systems.

The technology of transferring genes from one species and expressing them in another is made possible because the DNA of all living organisms is chemically similar in that it is composed of long chains containing the same four nucleotides. Nucleotide sequences are arranged in codons (triplets) which code for specific amino acids with the coding relationship between the amino acid and nucleotide sequence being essentially the same for all species of organisms. The DNA is organized into genes which are comprised of control regions which mediate initiation of expression of the gene and coding regions. These control regions are commonly referred to as "promoters." An enzyme, called RNA polymerase, binds to the promoter region and is either activated or in some way is signalled so that it travels along the coding region and transcribes the encoded information from the DNA into messenger ribonucleic acid (mRNA). The mRNA contains recognition signals: signals for ribosome binding, signals for translational start and stop, and for polyadenylation. Cellular ribosomes then translate the nucleotide codon information of the mRNA into protein with an amino acid sequence specified by the nucleotide codon sequence.

The general use of restriction endonucleases and the ability to manipulate DNA sequences has been greatly improved by the availability of chemically synthesized double stranded oligonucleotides containing desired nucleotide sequences including useful restriction site sequences. Virtually, any naturally occurring, cloned, genetically altered or chemically synthesized segment of DNA can be coupled to any other segment by attaching an oligonucleotide containing the appropriate sequences or recognition sites to the ends of the DNA molecule. Subjecting this product to the hydrolytic action of the appropriate restriction endonuclease produces the requisite complementary ends for coupling the DNA molecules. While there are many possible variations in gene transfer schemes, it is important to note that the techniques are available for inserting DNA sequences in the proper location and orientation with respect to a promoter region to allow expression of those sequences.

Potentially, any DNA sequence can be inserted into a vector molecule to construct an artificial recombinant molecule or composite, sometimes called a chimera or hybrid DNA. For most purposes, the vector utilized is a duplex extra-chromosomal DNA molecule comprising an intact replicon such that the recombinant DNA molecule can be replicated when placed into bacteria or yeast by transformation. Vectors commonly in use are derived from viruses or plasmids associated with bacteria and yeast.

Because of the nature of the genetic code, the inserted gene or portions thereof will direct the production of the amino acid sequence for which it codes if the gene or gene portion is attached to a control region (promoter) which is capable of regulating expression in the cell in which the vector replicates. The general techniques for constructing expression vectors with cloned genes located in the proper relationship to promoter regions are described in the literature (e.g., See T. Maniatis, et al. (1982) *Molecular Cloning A Laboratory*

*Manual,* Cold Spring Harbor Laboratory, Cold Spring Harbor, N.Y.).

A number of vector systems utilizing the above-described general scheme and techniques have been developed for use in the commercial or experimental synthesis of proteins by genetically modified organisms. Many of these vector systems utilize prokaryotic bacterial hosts for vector replication and heterologous gene expression. Additionally, systems have been utilized which employ eukaryotic cells for vector replication and heterologous gene expression. Such systems are employed for hepatitis B virus surface antigen synthesis and for human tissue plasminogen activator synthesis.

Eukaryotic hosts are preferred for the production of some eukaryotic proteins which require modification after synthesis (i.e., glycosylation) to become biologically active. Prokaryotic cells are generally incapable of such modifications.

The use of virus vectors in eukaryotic hosts has been the subject of a considerable amount of recent investigation. Viral vector systems may suffer from significant disadvantages and limitations which diminish their utility. For example, some viral vectors are not able to achieve high enough levels of gene expression for economic protein production in costly eukaryotic cell culture systems. Some eukaryotic viral vectors are either pathogenic or oncogenic in mammalian systems, creating the potential for serious health and safety problems associated with accidental infection. Some virus vectors have severe limitations on the size of the heterologous gene that can be stably inserted into the virus particles.

As the genetic engineering technology becomes more sophisticated, there will be an increased interest in inserting more than one heterologous gene, i.e., genes coding for more than one protein, into a host cell to achieve coordinated expression and possibly to obtain coordinated activity of the various gene products.

An ideal viral vector should be capable of stably carrying a large segment of heterologous DNA, efficiently infecting cells and converting virtually all the protein biosynthesis of the infected cell to the high level expression of the foreign gene. A virus that appears to be well suited as a vector for the propagation and high level expression of many heterologous genes in a higher eukaryotic environment is the baculovirus *Autographa californica* nuclear polyhedrosis virus (AcMNPV). (See Miller, L. K. (1981) "Virus Vector for Genetic Engineering in Invertebrates," In *Genetic Engineering in the Plant Sciences,* N. Panopolous (ed.), Praeger Publ., N.Y., pp. 203-224; U.S. Pat. No. 4,745,051.)

The baculovirus group includes the subgroups of nuclear polyhedrosis viruses (NPV) and granulosis viruses (GV); baculoviruses infect only arthropod hosts. The virus particles of NPV and GV are occluded in proteinaceous crystals. In occluded forms of baculoviruses, the virions (enveloped nucleocapsids) are embedded in a crystalline protein matrix. This structure, referred to as an inclusion or occlusion body, is the form found extraorganismally in nature and is responsible for spreading the infection between organisms. The subgroup NPV produces many virions embedded in a single, large (up to 5 micrometers) polyhedral crystal, whereas the subgroup GV produces a single virion embedded in a small crystal. The crystalline protein matrix in either form is primarily composed of a single 25 to 33 kDa polypeptide which is known as polyhedrin or granulin in NPV or GV, respectively.

More general information on the subject of baculovirus structure and the process of infection is available in the following reviews: Carstens (1980) "Baculoviruses—Friend of Man, Foe of Insects?," *Trends and Biochemical Science,* 52:107-10; Harrap and Payne (1979) "The Structural Properties and Identification of Insect Viruses" in *Advances in Virus Research,* Vol. 25, M. A. Lawer et al. (eds.), Academic Press, New York, pp. 273-355; and Miller, L. K. (1981) supra.

Baculovirus helper-independent viral vectors are particularly useful for the high-level production of biologically active eukaryotic proteins. Expression levels for some foreign genes have been reported to be 10% to 25% of the total protein of the recombinant infected cell. Appropriate post-translational modifications, including signal peptide cleavage, glycosylation, phosphorylation, oligomerization, complex formation, isolation and proteolysis, have been reported for a variety of different heterologous proteins produced using this expression system.

The baculovirus expression vectors described to date use very late promoters, such as the polyhedrin or polypeptide 10 (p10) promoters to drive foreign gene expression. (Reviewed by Luckow and Summers (1988) "Trends in the Development of Baculovirus Expression Vector," *Bio/Technology* :47-55 Miller, L. K. (1988) "Baculoviruses as Gene Expression Vectors," *Ann. Review of Microbiology,* 42:177-199.) These promoters are regulated during the course of virus infection and are activated very-late in the infectious process usually beginning 18 to 24 hours post-infection. The polyhedrin and p10 genes are not essential for replication in cell culture, so the gene can be replaced with the heterologous gene of interest without interfering with the production of the budded form of the virus. The replacement of the polyhedrin gene, however, does interfere with the formation of the occluded form of the virus. The absence of the occluded virus in recombinant plaques provides a useful although somewhat tedious phenotypic selection for the recombinant viruses. It also places limitations on the ability to use the recombinant viruses for less expensive mass protein production in insect larvae.

The economic value and general utility of a baculovirus vector is strongly dependent on the nature of the promoter used to drive heterologous gene expression. The polyhedrin promoter is currently the promoter of choice for the production of high levels of protein. However, even higher levels of protein production are often necessary for economic feasibility. In addition to the need for high productivity, vectors are needed which can express more than one heterologous gene. The disadvantage to such vectors is that they are often genomically unstable if promoter sequences are duplicated within the vector. To minimize such instability, a different promoter must be employed for each heterologous gene to be expressed. These promoters must be different (nonhomologous) from naturally occurring viral promoters within the vector to more fully avoid genomic instability problems. Vectors should also have the ability to include promoters that express genes at an earlier stage of protein production to improve protein quality and to ensure that the protein has the necessary post-translational modifications to confer biological activity or immunological authenticity. Such post-translational modifications appear to decline during the very late phase of infection when the very late promoters of AcMNPV vectors, such as polyhedrin and p10, are activated.

What are needed are modified or synthetic promoter regions which will cause significantly increased expression of the heterologous gene in the baculovirus system or which will allow the production of high quality protein. The new promoters should be flexible enough so that either a single heterologous gene or a series of heterologous genes can be inserted into the vector system so that various proteins can be produced at the same or at different times. In addition, the polyhedrin gene should be present if the virus is to be administered orally to the appropriate insect host.

SUMMARY OF THE INVENTION

The present invention provides an improved means of employing baculovirus gene expression vectors for expression of heterologous genes by placing the genes under the control of novel or modified promoters; preferably a novel promoter which promotes high level expression of a gene and allows the proper post-translational modifications of the gene product in insect cells. More specifically, in a preferred embodiment, the present invention comprises providing a modified baculovirus promoter to which a heterologous gene is attached. The promoter is inserted into a virus via a transplacement plasmid or by direct insertion to produce a recombinant virus vector which can be used to infect suitable host cells. The infected host cells are then used to produce the heterologous gene product.

In accordance with the present invention, a method and composition are provided for improving the level of expression of a heterologous gene or a collection of genes. The present invention includes a novel promoter which contains a modification of a natural baculovirus promoter or a synthetic modified promoter functional in a baculovirus expression system. The new promoter may be a combination promoter such as a promoter with a double start site (i.e., two ATAAG's) or a combination of two different promoters such as an early/very late promoter or a late/very late promoter. It is contemplated that the present invention also includes foreign gene placement in a novel location or genomic orientation. All the aforementioned promoters are termed "modified baculovirus promoters" herein.

A modified baculovirus promoter of the present invention has one or more features selected from the group consisting of an ATAAG sequence flanked by a very A+T rich region, an upstream activator sequence, similar to those of linker scan promoters LSXVI, LSXIV and LSXVII, of about 10bp of GC-rich sequence, placed from about 10 to about 30bp upstream of the transcription start site, a polyadenylation site ($A_2UA_3$ site) in the orientation opposite to desired transcription to block antisense transcripts which may originate from fortuitous TAAG sequences in the foreign gene, and selected components of one or more of three very strong late promoters (vp39, p10, and p6.9), and/or of the very strongly expressed very late genes (polyhedrin and p10). The selection of those components is based on their presence or conservation in untranslated leader sequences of abundantly expressed late and very late genes. An upstream activator sequence of a modified promoter is a sequence which acts to increase the level of transcription at a transcription start site located downstream therefrom. For use with a late or very late promoter in a baculovirus expression vector, the upstream activating sequence is a GC-rich sequence, with a nucleotide composition of at least about 60% G+C.

The modified promoter of the present invention shares only limited sequence homology or continuity with any other AcMNPV promoter. A major advantage of the novel promoter is that it can be stably incorporated at any region in the AcMNPV genome without concern for recombination with other regions of the AcMNPV genome. The modified promoter may also be designed to be stronger than the polyhedrin promoter.

The modified promoter of the present invention has been incorporated into several different transplacement plasmids by methods well known to those of ordinary skill in the art. For example, plasmid pSynVI contains the synthetic promoter in place of the EcoRV to KpnI fragment within AcMNPV sequences between 3.1 to 6.16 map units. According to one aspect of the present invention, the orientation of the promoter is such that the direction of expression will be opposite that of normal polyhedrin gene expression, thus taking advantage of the potential increase in gene expression when foreign genes are placed in this orientation. Foreign genes can be placed within the multicloning site of this plasmid and recombinant viruses can be identified on the basis of their occlusion negative phenotype.

A second transplacement plasmid, pSynVI+wtp, contains the synthetic promoter (including a multicloning site for passenger gene insertion) as well as an intact polyhedrin gene under the control of the wild-type polyhedrin promoter. When cotransfected with DNA from a polyhedrin-deficient mutant virus, this transplacement plasmid allows construction (or formation) of a recombinant virus that directs the production of both polyhedrin and the foreign gene product. The benefit is two fold: the recombinant virus has an easily visible and rapidly selectable (occlusion positive) phenotype, and the recombinant virus can infect insects orally. Thus it can be easily employed for mass production in insect larvae.

The transplacement plasmids can be further manipulated in any number of additional ways which may increase expression in different situations. For example, it may be useful to include a polyadenylation signal within the multicloning site and downstream from the foreign gene insert so that efficient polyadenylation occurs if an effective polyadenylation site is not included in the foreign gene insert. Portions of the multicloning site which are not used in transplacement plasmid construction may be deleted to improve expression since an A+T rich leader and an AACAAT sequence near the ATG seem to be preferred by highly expressed baculovirus genes (i.e., vp39, p10 and p6.9).

The ability to construct a modified promoter from linker scan modifications or from component parts of other promoters is a novel approach to promoter design. Most of the components of the novel promoter have been placed in one logical order. It is likely that the order of the components of the untranslated leader has flexibility.

Thus in accordance with the present invention, a modified promoter is provided that will allow multiple heterologous genes to be expressed with one vector.

An object of the present invention is to provide baculovirus vectors with modified promoters that will allow more than one heterologous genes to be expressed within one vector.

It is yet another object of the present invention to provide a modified promoter that is sufficiently different in sequence from other promoters in the virus so as to substantially eliminate the possibility of homologous recombination and subsequent deletion or inversion of a portion of the viral genome.

It is yet another object of the present invention to provide a recombinant baculovirus expression vector that can be fed orally to the appropriate insect host, thereby allowing the insect host-viral vector system to produce the desired heterologous protein.

It is yet another object of the present invention to provide an expression vector system in the baculovirus system that will allow increased expression of heterologous proteins when compared to the polyhedrin system.

These and other object features and advantages of the present invention will become apparent after a review of the following detailed descriptions of the disclosed embodiments and the appended claims.

Any baculovirus capable of replication in cultured host cells is useful for conversion into a vector of this invention. Preferably the baculovirus used is a nuclear polyhedrous virus, and more preferably is *Autographa/californica*.

The vectors of this invention may be prepared by genetic engineering technologies known to the art, preferably insertion of chimeric genes comprising the modified promoters of this invention in combination with heterologous genes placed under regulatory control of said promoters into the genome of a baculovirus by homologous recombination in an area of said genome able to tolerate said insertion without interference with the replication functions of said baculovirus, all as will be readily apparent to those skilled in the art.

The host cells useful for expression of the heterologous genes under control of the modified promoters of this invention are insect cells in which the baculovirus vectors of this invention are capable of replication and expression, all as known to the art, and include cultured insect cells in vitro and insect larvae.

The conserved sequences of the late and very late promoters of this invention may be readily identified by those skilled in the art and are exemplified, e.g., in Table 1.

Any upstream activating sequence known to those skilled in the art may be used to enhance expression of the chimeric genes of this invention. A preferred upstream activating sequence of this invention is a G+C-rich sequence of about 10 bp, more preferably a HindIII site linker as exemplified by the sequence CCAAGCTTGG.

Any transplacement plasmid known to the art which has sequences flanking the chimeric gene(s) of the present invention which are homologous to the baculovirus which is to serve as the expression vector can be used in the practice of the present invention. It is understood that those homologous flanking sequences must be sufficiently long to mediate the homologous recombination of the chimeric gene from the transplacement plasmid to the baculovirus vector. The transplacement plasmids exemplified by the present invention are pEV55 and derivatives thereof.

DETAILED DESCRIPTION OF THE DISCLOSED EMBODIMENTS

In accordance with the present invention, a method and composition are provided for improving the expression of a gene or collection of genes in a baculovirus expression vector. More particularly, the present invention provides a plasmid containing a novel promoter that is used to drive foreign gene expression and improve the quality of the proteins produced during infection. The novel promoter may optionally contain a synthetic promoter, modifications of a natural promoter, and/or combinations of natural, modified or synthetic promoters. The novel promoter may also comprise a combination promoter, including but not limited to, a promoter with a double start site (i.e., two ATAAG's) or a combination of two baculovirus different promoters such as an early/very late promoter or a late/very late promoter. It is contemplated that the present invention also includes promoter-foreign gene placement in a novel location or a genomic orientation.

The insect baculovirus *Autographa californica* nuclear polyhedrosis virus (AcMNPV) is now widely employed as a gene expression vector (reviewed by Luckow and Summers, "Trends in the Development of Baculovirus Expression Vectors," *Bio/Technology* 6:47–55, 1988; Miller, L. K., Baculoviruses as Gene Expression Vectors, *Ann. Review of Microbiology*, 42:177–199, 1988). The helper-independent viral vector systems generally involve the insertion of the foreign gene to be expressed into the AcMNPV genome under the control of a very late viral promoter, either the polyhedrin promoter or the p10 promoter. These two novel promoters are considered particularly useful because they mediate high level transcription of their respective genes, resulting in high steady state levels of mRNA during the last phase of the infection process, the occlusion phase. Occlusion, the embedding of viral particles in a paracrystalline protein matrix, is nonessential for virus propagation in cell culture although it is required for the efficient oral infection of host larvae. Thus, the replacement of occlusion phase-specific genes and the high level expression of heterologous genes instead of the occlusion genes have no observable impact on nonoccluded virus (budded virus) production which is responsible for infection in cell cultures.

The baculovirus expression system was originally developed with very little knowledge of baculovirus gene organization or the nature of baculoviral promoters (Miller, L. K., 1981 supra. One of the first transplacement plasmids developed for a polyhedrin promoter-based vector system was pAc373; it was widely used before it was reported that some of the sequences essential for normal levels of gene expression were absent in this vector (Matsuura et al. (1987) "Baculovirus expression vectors: The requirements for high level expression of proteins, including glycoproteins" J. Gen. Virol. 68:1233–1250). Transplacement plasmids, which include the nucleotides immediately upstream of the +1 (A of the ATG) position of the polyhedrin gene are now recommended for vector use (Luckow and Summers (1988) supra: Miller, L. K. (1988) supra). Nucleotides downstream of the +1 position (i.e., within the polyhedrin open reading frame) are not required for optimal transcriptional efficiency (Carbonell et al. (1988) "Synthesis of a gene encoding an insect-specific scorpion neurotoxin and attempts to express it using baculovirus vectors," Gene, 73:409–418).

Linker scan mutational analysis of the region immediately upstream of the polyhedrin coding sequence by the present inventor has revealed several unique features of this region. The primary determinant of promoter activity resides within the sequence TAAGTATT at the transcriptional start site located at −50 with respect to the ATG (+1, +2, +3) at the translation start site. The sequences flanking the transcriptional start site influence the levels of transcription and reporter gene expression in more subtle ways. Linker replacement of the sequences 10 to 30 bases upstream of the TAAGTATT increases the levels of transcription and gene expression as much as 50% while linker replacements between TAAGTATT and the +1 position (i.e., within the sequences specifying the untranslated leader region) down-regulate promoter activity by 2 to 10 fold. Reversing the genomic direction of the reporter gene and 93 nucleotides of the polyhedrin "promoter" (i.e., +1 to −92) provided equivalent or slightly higher levels of reporter gene expression than that observed in the natural direction. None of the mutations altered the temporal regulation of gene expression; all gene expression from the modified polyhedrin promoters was restricted to the very late phase (Rankin et al. (1988) "Eight Base Pairs Encompassing the Transcriptional Start Point and the Major Determinants for Baculovirus Polyhedrin Gene Expression," Gene 70:39–49, incorporated herein by reference).

Although it has been assumed that the very late polyhedrin and p10 promoters probably represent the optimal promoters for foreign gene expression, the comparative ability of late promoters to drive foreign gene expression has never been tested directly. The two most abundantly expressed late virus structural genes encoding vp6.9 (core) and vp39 (capsid) have been located, sequenced, and transcriptionally mapped (Wilson et al. (1987) "Location, transcription, and sequence of a baculovirus gene encoding a small arginine-rich polypeptide," J. Virology, 61:661–666). These genes are transcribed abundantly at 12 hrs post-infection, and approximately 12 hrs before transcription from the strong polyhedrin promoter. The products of the vp6.9 and vp39 genes are required for both the budded and occluded forms of the virus. Thus, their expression would be expected to continue through very late times post-infection and provide a longer period for foreign gene expression than the polyhedrin or p10 promoters. Specific expression of foreign gene products at very late times has been considered to be preferable for expression of those foreign genes whose products might interfere with budded virus synthesis (Miller, L. K. (1981) supra).

However, many heterologous gene products do not adversely affect virus synthesis, and earlier high level expression would be advantageous from a production perspective. Expression during the late phase is also preferable to the very late phase for efficient post-translational modification. Host nuclear mRNA transcripts decrease dramatically between 12 and 24 hrs post-infection and the post-translational modification, which is probably mediated primarily by host gene products, appears to become inefficient during the very late phase of expression. The inventor has found that the late capsid promoter, i.e., the vp39 promoter, is excellent for driving foreign gene expression during the late phase; it outperforms the polyhedrin promoter between 12 and 24 hours post-infection by approximately 5 to 8 fold.

The present invention includes the improvement of baculovirus gene expression vectors to provide higher levels of foreign gene expression than currently provided by very late promoters such as natural viral polyhedrin and p10 promoters. The present invention also includes two different approaches: (1) modification of the upstream sequences flanking the transcriptional start point of the polyhedrin promoter and (2) utilization of the late vp39 (capsid) promoter or late/very late promoter combinations to drive foreign gene expression. Reversing the genomic orientation of the promoter and foreign gene seems to have very little impact on the levels of gene expression and has allowed the design of plasmids for the simultaneous transplacement and the expression of two or more foreign genes directed by a single baculovirus expression vector.

In addition, according to the present invention, novel synthetic promoters have been designed which share minimal DNA sequence homology with other natural baculoviral promoters.

Such promoters are useful for the expression of more than one foreign gene using a single recombinant virus and eliminate the need for duplicating a natural viral promoter sequence within the vector, thereby minimizing the potential for genomic instability due to homologous recombination between the repeated promoter sequences.

As part of the present invention, transplacement plasmids are described which mediate the formation of baculovirus expression vectors capable of: (1) elevated levels of gene expression, (2) simultaneous expression of two passenger genes, (3) expression of passenger genes during the late as well as very late phases, and/or (4) simultaneous expression of both a passenger gene and the polyhedrin protein.

Transplacement plasmids facilitate the insertion of a foreign gene into the baculovirus genome by providing useful restriction sites for inserting the foreign gene(s) (i.e., a multicloning site at the appropriate site downstream of a promoter), and flanking sequences of viral DNA from the region of the viral genome into which the foreign gene(s) is to be integrated. The flanking viral sequences provide sites for cell-mediated homologous recombination between nonrecombinant viral DNA and recombinant transplacement plasmids to yield the recombinant viral vector.

Figure 10:
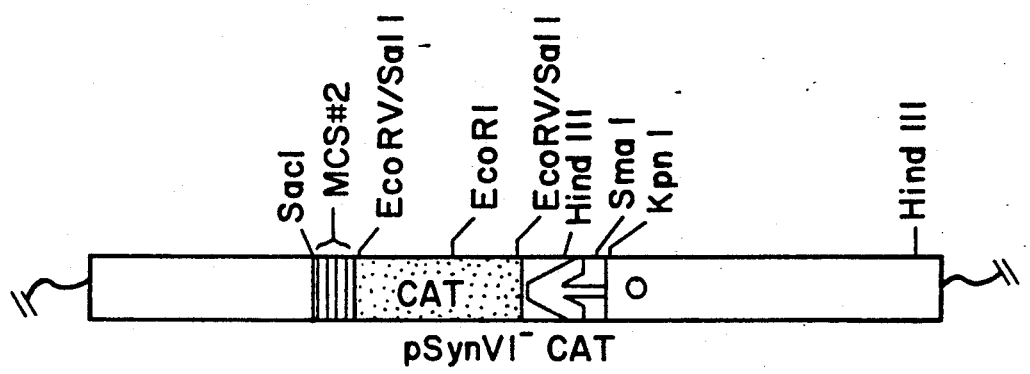
FIG. 10 is a schematic representation of the plasmid pSynVI-CAT.

The inventor has found that certain linker scan mutations upstream of the polyhedrin TAAGTATT increase transcription and increase foreign gene expression relative to the wild-type polyhedrin promoter (Rankin et al. (1988) supra). The plasmids phcLSXIV, shown schematically in FIG. 1, and pEVmodXIV, which carries the same promoter and basic multi-cloning site as phcLSXIV but lacks the CAT gene, contain a linker scan mutant promoter, currently referred to as the LSXIV promoter. Viruses derived from peEVmodXIV, or derived from phcLSXIV, provide higher levels of reporter gene (CAT) expression than other known linker scan modifications. Expression from viruses carrying the CAT reporter gene under the control of the LSXIV promoter has been shown by the inventor to be 50% higher than that from the polyhedrin promoter (i.e., compared to CAT gene expression from recombinant viruses derived from phcwt, shown schematically in FIG. 10, which contains a wild-type polyhedrin promoter).

Figure 1:
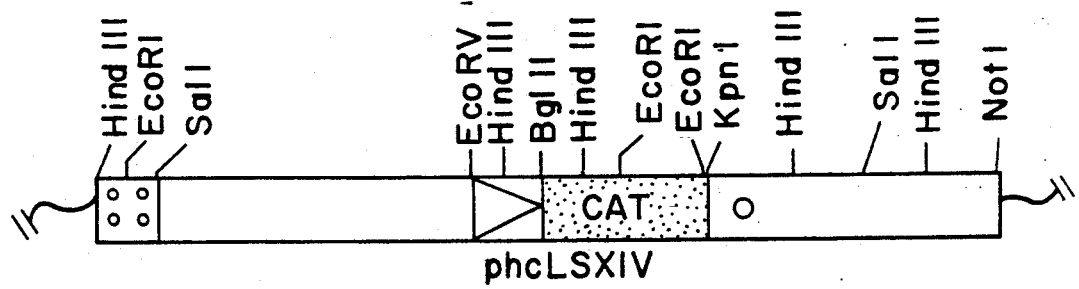
FIG. 1 is a schematic representation of the plasmid designated phcLSXIV.

Thus, preferred embodiments of the present invention include several plasmids which contain promoters having various modifications upstream of the TAAGTATT sequences. The plasmid designated phcLSXIV, shown schematically in FIG. 1 is an example of a plasmid containing such modified promoters. Other plasmids of this nature include phcLSXVI and phcLSXVII (as shown in Table 5). These plasmids contain upstream modified promoters which causes elevated levels of foreign gene expression when incorporated into recombinant viruses.

As another preferred embodiment, the present invention includes plasmids containing a synthetic promoter. Synthetic promoters provide diversity in the nucleotide sequence of promoters used to drive heterologous gene expression and provide differences in the levels of foreign genes expressed. A sequence for a preferred synthetic promoter is described best by the DNA sequence shown in Table 1. (SEQ ID NO: 6). The arrow in the DNA sequence shows the start point and the direction of transcription. It is to be understood that there is much flexibility possible in arranging and ordering the components of the promoter and that the sequence shown in Table 1 (SEQ ID NO: 6) is only one example of an embodiment of the present invention.

Figure 2:
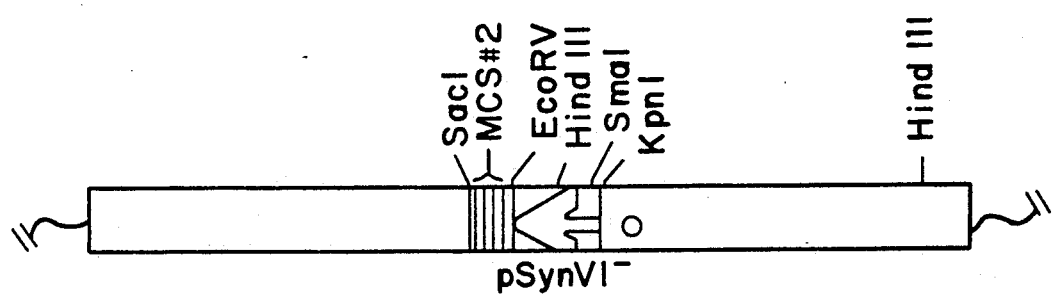
FIG. 2 is a schematic representation of the plasmid designated pSynVI-.

An example of a transplacement plasmid of the second preferred embodiment which includes the above-referenced synthetic promoter is shown in the general construction in FIG. 2. This plasmid, designated pSynVI-, is a transplacement plasmid carrying the synthetic promoter shown in Table 1 (SEQ ID NO: 6) and the multi-cloning site (MCS) termed MCS#2 herein. The MCS#2 sequence of pSynVI- is shown in Table 2 and in SEQ ID NO: 7 from nucleotide 93 through nucleotide 159. The orientation of the synthetic promoter is such that foreign gene expression will occur in the genomic orientation opposite that of the polyhedrin gene. This promoter construct drives heterologous gene expression at approximately 10%-20% of the level of the wild-type polyhedrin promoter.

Figure 3:
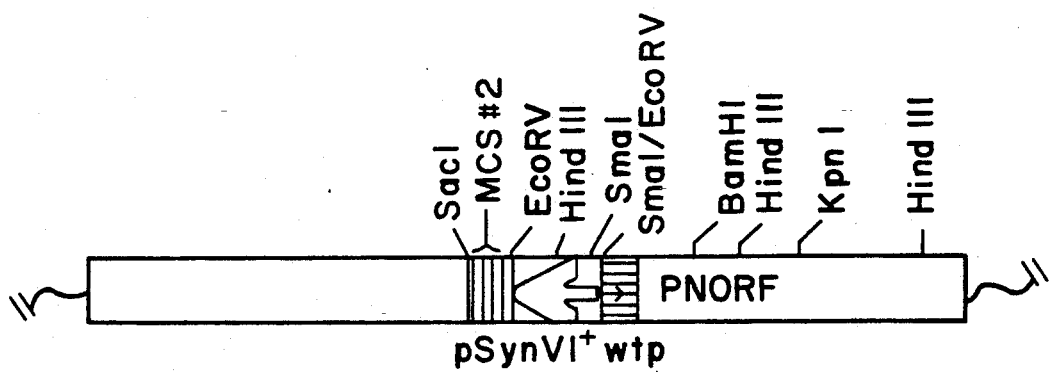
FIG. 3 is a schematic representation of the plasmid designated pSynVI+wtp.

Another example of the second preferred embodiment of the present invention is the plasmid designated pSynVI+wtp. The schematic representation of this promoter is shown in FIG. 3. This construct is a transplacement vector containing the synthetic promoter (SEQ ID NO: 6) described above and MCS#2 (see SEQ ID NO: 7, ) nucleotides as in the foregoing pSynVI- but also expressing the polyhedrin gene under wild-type polyhedrin promoter control. It is an example of a plasmid which is able to express two genes simultaneously. This plasmid provides the selectable occlusion positive phenotype and, because recombinant viruses are occlusion positive, they can be used to orally infect insects. This plasmid construction drives expression of the heterologous gene at approximately 10%-20% of the natural polyhedrin promoter.

Figure 4:
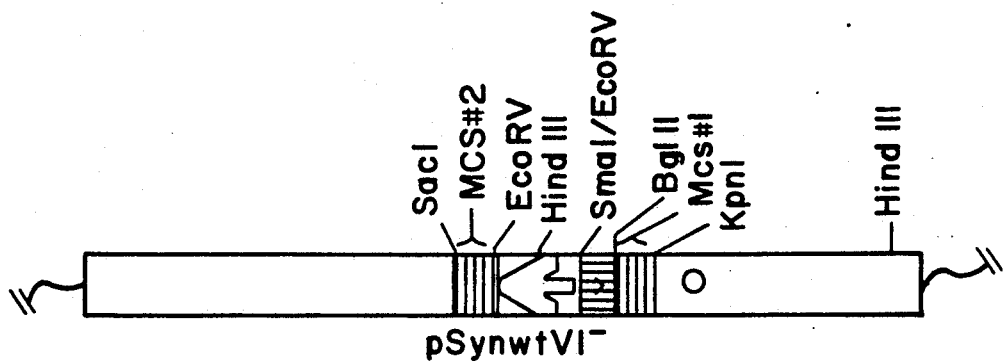
FIG. 4 is a schematic representation of the plasmid designated pSynwtVI-.

Another plasmid that is included as an example of the second preferred embodiment of the present invention is designated pSynwtVI- and is shown in FIG. 4. This is a transplacement plasmid containing both the polyhedrin promoter (with an MCS site, MCS#1) and a synthetic promoter (with a second MCS site, MCS#2), features which allow for the expression of two foreign genes. This transplacement plasmid is therefore an example of a two-gene expression vector. However, it is to be understood that it is not necessary to use the polyhedrin promoter because other synthetic promoters can be designed to replace the polyhedrin promoter based on principles noted for the synthetic promoter described above.

Figure 5:
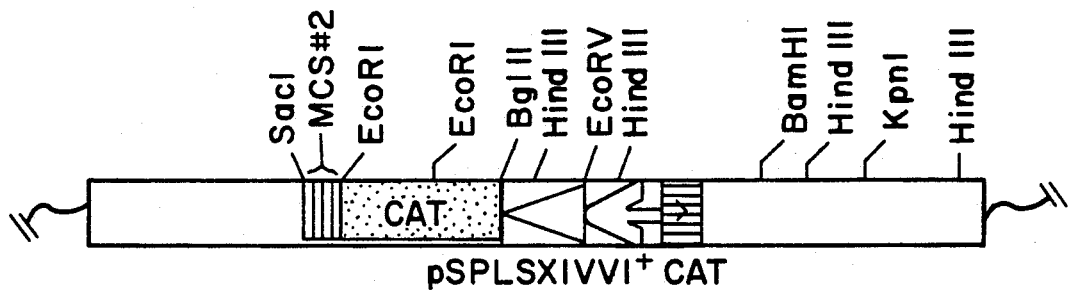
FIG. 5 is a schematic representation of the plasmid designated pSPLSXIVVI+CAT.
Figure 6:
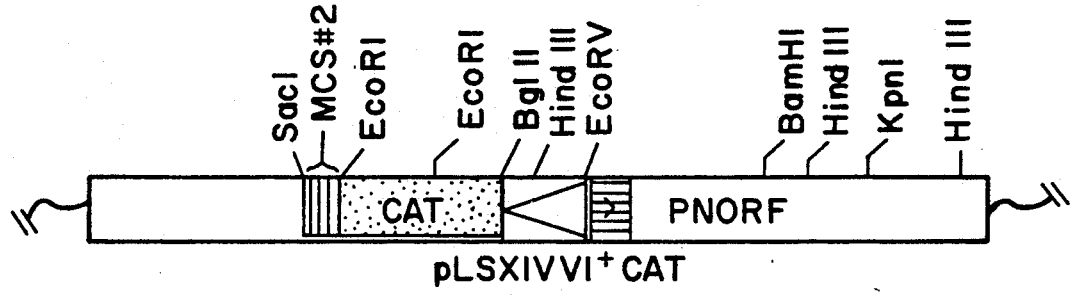
FIG. 6 is a schematic representation of the plasmid designated pLSXIVVI+CAT.

In a third preferred embodiment of the present invention, the plasmids contain a promoter or promoters in an orientation opposite to that of the naturally occurring promoter. The plasmids pSPLSXIVVI+CAT and pLSXIVVI+CAT (FIGS. 5 and 6) are plasmids with the pLSXIV promoter (see SEQ ID NO: 5) in the opposite orientation (with respect to the original polyhedrin direction). These plasmids are used to test CAT expression from the LSXIV promoter in opposite orientations. The pLSXIVVI+CAT plasmid has a tandem double promoter. CAT gene expression from the LSXIV promoter (SEQ ID NO: 5) in the opposite orientation has been found by the inventor to be similar to the levels achieved in the original orientation.

Figure 13:
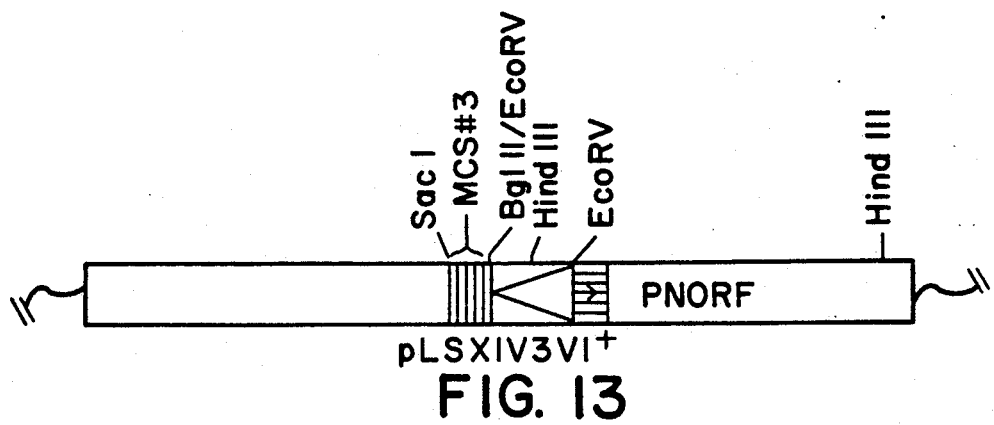
FIG. 13 is a schematic representation of the plasmid pLSXIV3VI+.

It is contemplated as part of the present invention that the promoters can be positioned in different genomic positions/orientations to give elevated levels of expression. The plasmids pSPLSXIVVI+CAT (FIG. 5) and pLSXIV3VI+ (FIG. 13) are two examples of high level expression promoters in opposite orientation.

A fourth preferred embodiment of the present invention includes plasmids containing the vp39 (capsid) promoter sequence. The DNA sequence of this promoter is shown in Table 3 SEQ ID NO: 8. The transplacement plasmids which can be used for testing reporter CAT expression include phc39 and pEVmod39. The vp39 promoter provides approximately 5 to 120 fold higher levels of expression during the period of time from 12 to 24 hrs post-infection than the naturally occurring polyhedrin promoter. It is contemplated that the present invention also includes a combination of late/very late promoters such as the polyhedrin and vp39 promoters which would provide earlier gene expression and higher final levels (total levels) of heterologous proteins. One obtains higher levels of expression at 12 hrs post-infection from the late promoters because they are being expressed earlier in the infection process (i.e., they turn on at 6 hrs post-infection rather than at 18 hrs post-infection as in the case of polyhedrin). The combination late/very late promoter ideally turns on at approximately 6 hrs post-infection and continues through 70 hr post-infection thus providing both late and very late gene expression.

Design of a synthetic promoter and a transplacement plasmid carrying the synthetic promoter The inventor has discovered that the major determinant for polyhedrin gene expression appears to be located within the sequence ATAAGTATT. Transcription of this abundantly transcribed late gene also initiates within an ATAAG sequence flanked by an A+T rich region (Wilson et al., 1987, supra). A novel baculovirus promoter has been designed which lacks minimal extended sequence homology to other viral promoters by combining short sequence motifs common to other abundantly expressed late and very late genes. Two additional features incorporated in the design of the novel promoter include: an LSXIV linker, in the context of a G+C-rich region upstream of the ATAAG and a TTTATT sequence within the untranslated region near the ATG. The TTTATT serves as a polyadenylation signal for any transcripts initiating in the opposite orientation from ATAAG sequences which occur by chance in the foreign gene insert.

The inventor has found that late and very late promoters contain an ATAAG at the most abundant transcriptional start points. This sequence is important for polyhedrin expression and promoter activity. In addition, linker scan mutational analysis of the polyhedrin promoter shows that nucleotides throughout the untranslated leader region appear to contribute to optimum gene expression. The sequences specifying the untranslated leader regions of four promoters of the most abundantly expressed genes of AcMNPV, namely the late gene encoding the major capsid protein (p39), the late gene encoding the basic core protein (p6.9), the very late gene encoding p10 and the polyhedrin gene have been aligned. All contain ATAAGs in the context of an A+T-rich region.

Several short segments found in two or more of the promoters have been chosen as component parts of the synthetic promoter (Table 1, SEQ ID NO: 6). The longest segment common to two or more promoters is nine nucleotides, TAAATTACA, found in both the p10 and p6.9 promoters. The sequence ACAAT has been found near the ATG of 3 of 4 promoters but not polyhedrin), TACTGT was found in both the polyhedrin and p10 promoters, TTTGTA has been found in both the p10 and polyhedrin promoters, TTTGTA has been found in both the p10 and polyhedrin promoters, and TCAANTCA has been found in the p10 and the p39 promoters. In addition, all the promoters contain stretches of at least 3 T's, usually flanked by A's, and stretches of at least 3 A's, usually preceded by a pyrimidine. All these components have been designed into the model synthetic promoter. The components have been placed to minimize length; for example, the T stretches and A stretches have been placed just downstream of the ATAAG to also serve as an A+T rich region downstream of the ATTAG. However, the ACAAT sequence has been placed near the 3' restriction site (BglII) which serves to link the promoter to a multicloning site and the TTTATT (polyadenylation signal in reverse) has been positioned flanking this sequence to encourage termination of reverse transcripts as far from the ATAAG as possible, thereby minimizing antisense RNA interference at the 5' end. The sequences of the two oligonucleotides which have been synthesized to construct the model synthetic promoter, referred to as the Syn promoter, are shown in Table 1, (SEQ ID NO: 6) along with the designations of the component parts.

The transplacement plasmid pSynVI- (FIG. 2) has the Syn promoter (SEQ ID NO: 6) driving expression in the opposite direction as the polyhedrin promoter. It also has a multicloning site (MCS#2) (SEQ ID NO: 7, nucleotides 93-159) with numerous useful restriction sites. It lacks 627 nucleotides encoding the N-terminus of polyhedrin, and thus the use of this transplacement plasmid results in recombinants with occlusion negative phenotypes.

The synthetic promoter and attached multicloning site (MCS#2) can also be moved to other plasmids for transplacement into other AcMNPV genomic locations using flanking restriction endonucleases (e.g., SacI downstream of MCS#2 and KpnI or SmaI upstream of the promoter).

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example I

All viruses are derived originally from AcMNPV L-1 (Lee and Miller (1978) "Isolation of genotypic variants of *A. californica* nuclear polyhedrosis virus," J. Virol. 27:754-767); and are plaque-purified and propagated in the *Spodoptera frugiperda* IPLB-SF-21 cell line (Vaughn et al. (1977) "Establishment of Two Insect Cell Lines From the Insect *Spodoptera frugiperda* (Lepidoptera: Noctuidae)" In Vitro 13:213-217 using methods described previously (Lee and Miller (1978); Miller et al. (1986) supra; "An insect baculovirus host-vector system for high-level expression of foreign genes," in *Genetic Engineering, Principles and Methods*, Vol. 8 J. Setlow and A. Hollaender (eds.), Plenum Press, N.Y., pp. 277-298, 1986.

CAT assays are performed and specific activities calculated as described previously (Carbonell et al. (1985) "Baculovirus-Mediated Expression of Bacterial Genes in Dipteran and Mammalian Cells," J. Virol. 56:153-160; Rankin et al. (1988) supra;. The CAT gene for all CAT-containing plasmids used in these studies was derived from pCM1CAT (LKB Biotechnology, Piscataway, N.J.) in which the CAT gene is inserted as a SalI cassette. *428

Example II

Figure 7:
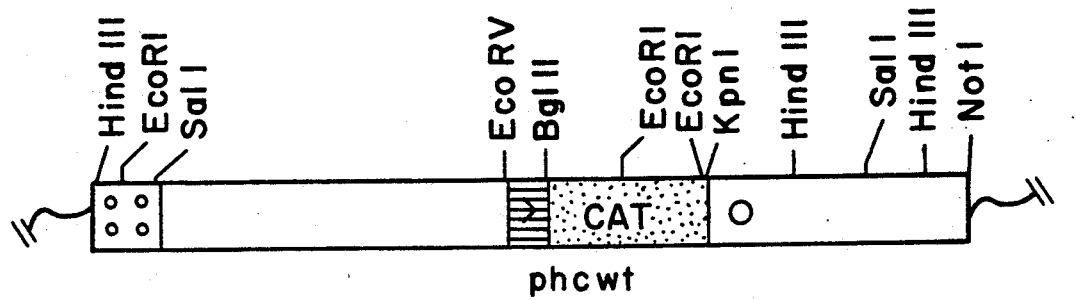
FIG. 7 is a schematic representation of the plasmid phcwt.
Figure 8:
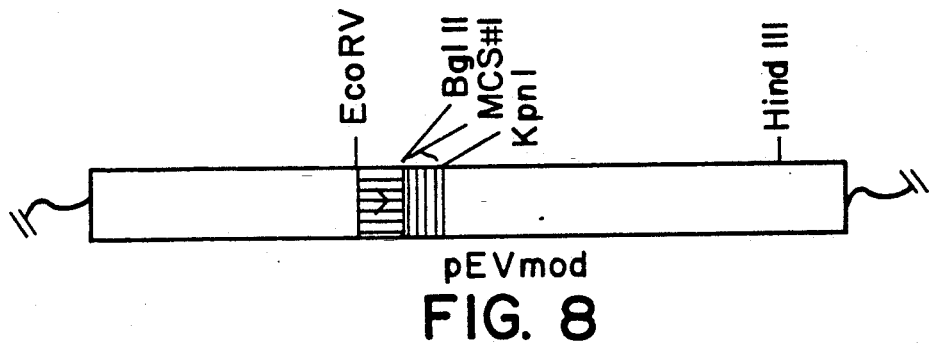
FIG. 8 is a schematic representation of the plasmid pEVmod.
Figure 9:
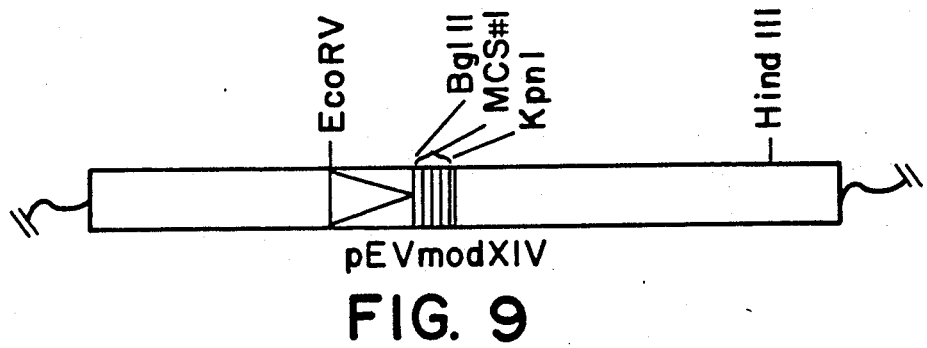
FIG. 9 is a schematic representation of the plasmid pEVmodXIV.

Construction of the pEVmodXIV transplacement plasmid (FIG. 9) is described. The previously described transplacement plasmid pEV55 (Miller et al. (1986) supra), which serves as the basis for constructing phcwt (FIG. 7), also serves as the starting plasmid for pEVmodXIV construction. The pEV55 plasmid contains AcMNPV DNA from 3.18 to 7.3 map units (mu). A multicloning site replaces polyhedrin coding sequences from +1 to +635. The numerous restriction endonuclease sites at the junction between the pUC vector portion of pEV55 and the SalI site of AcMNPV DNA at 3.18 limit the types of restriction sites which can be utilized in the multicloning site. Therefore, the sites at this junction are removed by digesting pEV55 with SmaI, which cuts at the vector junction, and by deleting approximately 70 nucleotides at the junction by the combined action of ExoIII and mung bean nuclease. Ligation at this deletion site results in the plasmid pEVdel. The viral sequences between 6.16 mu and 7.3 mu in pEVdel are deleted by digestion with BamHI (6.16 mu) and NotI (7.3 mu) at the right vector junction. Blunt end ligation at the deleted junction resulted in pEVmod (FIG. 8). The polyhedrin promoter (from the EcoRV at −92 to the BglII at +1) (see SEQ ID NO: 5) of pEVmod is replaced with the small EcoRV-BglII fragment of phcLSXIV (FIG. 1) resulting in the improved and convenient transplacement plasmid pEVmodXIV. Virus vectors derived from pEVmodXIV-based transplacement plasmids provide approximately 50% higher levels of expression than virus vectors derived from pEV55 or any other known plasmids.

Example III

Figure 15:
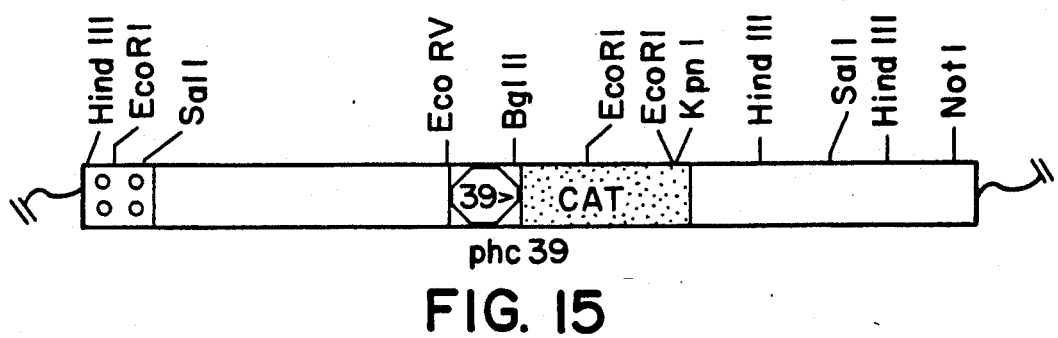
FIG. 15 is a schematic representation of the plasmid phc39.

Construction of the phc39 (FIG. 15) and pEVmod39 transplacement plasmids is described. A plasmid containing the vp39 promoter is first constructed as follows. The NarI to EcoRV fragment containing the vp39 promoter between 57.6 to 57.9 map units on the AcMNPV genome is cloned into the AccI and EcoRV sites of the plasmid vector Bluescript KS- (Stratagene, San Diego, Calif.). The resulting plasmid, pSTVNM, is cut at the XhoI and ApaI sites. The N-terminal sequences of the vp39 coding sequence are deleted with Exonuclease III and mung bean nuclease digestion. A BolII linker oligonucleotide is inserted into the gap using DNA ligase. One plasmid is selected which contains the BolII site at −2 relative to the ATG (+1, +2, +3) of vp39. To construct p39pro, the 458 bp capsid promoter region is excised from the previously selected plasmid using KpnI and EcoRV and is ligated into the plasmid Bluescript KS+ (Stratagene, San Diego, Calif.) which is also cut with KonI and EcoRV. To construct the transplacement plasmid phc39, the 458 bp EcoRV to BglII fragment of p39pro containing the vp39 promoter is excised and inserted into EcoRV and BglII digested phcwt, thus replacing the polyhedrin promoter of phcwt with the vp39 promoter region. The resulting transplacement plasmid, phc39 (FIG. 15) see also SEQ ID NO: 8 is used to construct viral vector vhc39. CAT gene expression using this vector is 5 to 10 times higher between 12 and 24 hours post infection than CAT gene expression from virus vectors carrying the CAT gene under polyhedrin promoter control. The earlier expression of the foreign gene provides for more efficient post-translational modification of the protein product. More convenient transplacement plasmids, such as pEVmod39 (not shown), can be derived easily from phc39 by replacing the CAT gene with a MCS containing BclII and KpnI termini (e.g., MCS#1).

Example IV

To construct the plasmid pSynVI- (FIG. 2), which contains the Syn promoter (SEQ ID NO: 6) and an adjoining multicloning site (MCS#2) (SEQ ID NO: 7, nucleotides 93–159) in place of the polyhedrin promoter, the two Syn promoter oligonucleotides shown in Table 1 are annealed, the duplex is purified by polyacrylamide electrophoresis, and is inserted into the KpnI- and EcoRV-digested Bluescript plasmid vector pBSKS- (Stratagene, San Diego, Calif.), which lacks the SmaI restriction site in the multicloning site. This allows the forced cloning of the oligonucleotide into the multicloning site of the Bluescript plasmid and the regeneration of both the EcoRV and KpnI sites.

The portion of the multicloning site of this plasmid from the EcoRV to the SacI site contains, in order, EcoRV, EcoRI, PstI, BamHI, SpeI, XbaI, NotI, SacII, and SacI sites. The synthetic promoter and this multicloning site are removed from the Bluescript vector by ordered digestion with SacI, mung bean nuclease, and KpnI. The small fragment is gel purified and inserted into the large, gel-purified fragment of KpnI- and EcoRV digested pEVmod (FIG. 8). The sequence of the promoter from the SmaI site through the flanking multicloning site, referred to as MCS#2, is determined by sequencing. The sequence is shown in SEQ ID NO: 7 and Table 2. The SacI site is regenerated unexpectedly and fortuitously during the cloning process; the action of mung bean nuclease downstream of the SacI site accounts for the observed junction.

A pSynVI- plasmid containing the reporter CAT gene is constructed to measure the level of gene expression of the pSynVI- plasmid by measuring the CAT gene expression of the constructed CAT-containing plasmid.

In constructing the pSynVI-CAT plasmid (FIG. 10), the CAT gene is excised from pCM1CAT with SalI, blunt-ended with mung bean nuclease, and inserted into pSynVI- cut with EcoRV. Orientation is checked using the EcoRI site in the N-terminal portion of the CAT gene. The corresponding viral vector, vSyn VI-CAT, provides CAT expression at levels approximately 10–20% of the levels observed for viral vectors expressing CAT under polyhedrin promoter control. Although not as high as polyhedrin promoter expression, this level of expression from a component synthetic promoter is significant. The Syn promoter and others derived by the combinatorial approach will be useful for balanced expression of two different foreign genes and/or the expression of genes encoding proteins controlling specific post-translational modifications.

Example V

For some applications, it is useful for a transplacement plasmid to transfer genetic information to form a recombinant virus which allows both foreign gene expression and polyhedrin gene expression. Expression of both genes results in occlusion, which permits efficient oral infection of insect larvae for inexpensive, bulk protein production. Furthermore, production in insect larvae allows expression in differentiated insect cells, including the fat body which constitutes a major secretory tissue of the insect and may provide more efficient post-translational modification than that found in available lepidopteran cell lines such as SF9 cells.

Thus, the pSynVI- (FIG. 2) is modified to produce a transplacement plasmid, pSynVI+wtp (FIG. 3), which allows simultaneous, high level expression of both polyhedrin and the foreign gene. An additional advantage of pSynVI+wtp is the ability to select recombinant viruses as occlusion positive plaques if the DNA of a polyhedrin deletion mutant (or a polyhedrin/β-galactosidase fusion mutant) is used in the initial co-transfections of host cells with viral DNA and transplacement plasmid.

The pSynVI+wtp transplacement plasmid is constructed by digesting a plasmid carrying the EcoRI-I fragment of the AcMNPV genome, with EcoRV and KpnI to remove the polyhedrin promoter and N-terminal polyhedrin region. The approximately 0.7kb EcoRV/KpnI fragment is gel-purified and inserted into pSynVI- which had been digested with SmaI and KpnI. Ligation eliminates the SmaI and EcoRV sites while regenerating the KpnI site found in the polyhedrin coding region. More specifically, the polyhedrin promoter and N-terminal coding sequences from EcoRV (−92) to KpnI (+635) are inserted into pSynVI- to produce the transplacement plasmid pSynVI+wtp. Polyhedrin mRNA is thus transcribed in its normal orientation under the control of its normal promoter while the foreign gene is inserted at the multicloning site under synthetic promoter control and is transcribed in the opposite direction to polyhedrin. The features of the plasmid are illustrated in FIG. 3. The sequence of the EcoRV/SmaI junction, the synthetic promoter, and the multicloning site (MCS#2) are shown in Table 1and 2 (SEQ ID NOS: 6 and ).

Figure 11:
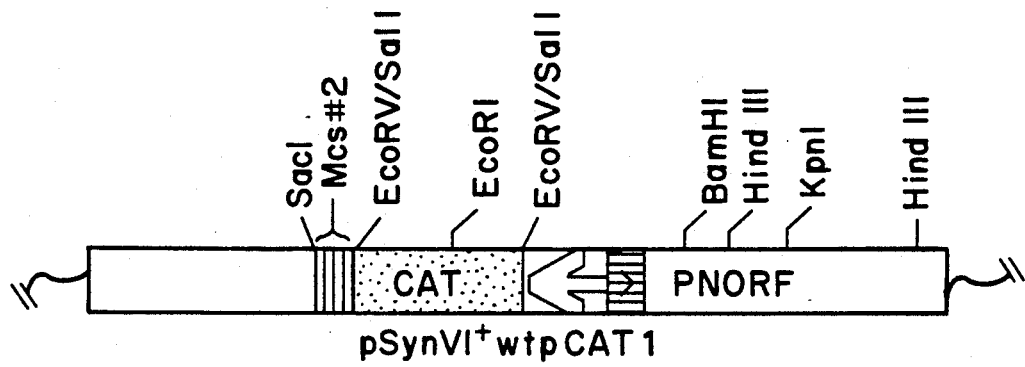
FIG. 11 is a schematic representation of the plasmid pSynVI+wtpCAT1.

To test the efficacy of the transplacement vector pSynVI+wtp, the reporter CAT gene is inserted into the MCS of pSynVI+wtp (FIG. 3) at the EcoRV site resulting in the plasmid pSynVI+wtpCAT1 (FIG. 11). To construct pSynVI+CAT1, the blunt-ended CAT-containing SalI fragment of pCM-1CAT is inserted into EcoRV-digested pSynVI+wtp. The ability of the Syn promoter to drive reporter CAT gene expression at the same time as polyhedrin gene expression is tested by isolating the recombinant virus vSynVI+wtpCAT1 and comparing levels of CAT expression with the levels obtained with vSynVI-CAT. No significant difference in CAT gene expression is observed between these two virus vectors showing that simultaneous expression of the polyhedrin gene did not impair foreign gene expression. The polyhedrin gene is also being abundantly expressed since the recombinant virus vSynVI+wtpCAT1 produces high levels of occlusion bodies.

Example VI

Construction of transplacement plasmid pSynwt VI- (FIG. 4) is described. This plasmid has two promoters in a back-to-back relationship allowing simultaneous transplacement of two heterologous genes and concerted expression of the two genes by a single vector. The pEV55 EcoRV-KpnI fragment, containing the polyhedrin promoter and multicloning site MCS#1, was inserted into pSynVI- which had been digested with SmaI and KpnI.

Figure 12:
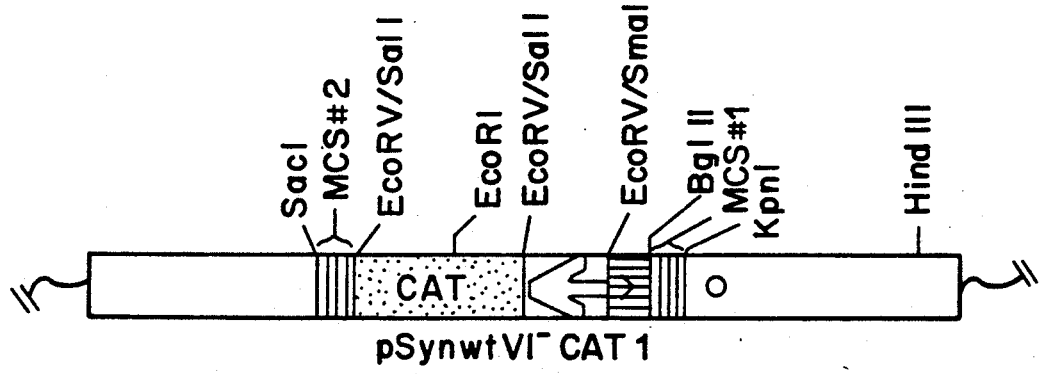
FIG. 12 is a schematic representation of the plasmid pSynwtVI-CAT1.

A pSynwtVI- plasmid containing the reporter CAT gene is constructed to provide a measure of gene expression of pSynwtVI-. The plasmid is pSynwtVI-CAT1 (FIG. 12). To construct pSynwtVI-CAT1, the blunt ended CAT-containing SalI fragment of pCM-1CAT is inserted into EcoRV-digested pSynwtVI-. The equivalent virus vector vSynwtVI-CAT1 expresses CAT activity at 10-20% of the levels observed for vectors expressing CAT under polyhedrin promoter control.

Example VII

Construction of the pSPLSXIVVI+CAT and pLSXIVVI+CAT transplacement plasmids (FIG. 5 and 6) are described. To construct pSPLSXIVVI+CAT, the CAT gene and attached LSXIV promoter (SEQ ID NO: 5) is removed from phcLSXIV (FIG. 1) by KpnI digestion (and blunt ended with mung bean nuclease) and EcoRV digestion, and then inserted into EcoRV-digested pSynVI+wtp. This places the LSXIV promoter in tandem with the synthetic promoter (SEQ ID NO: 6). The plasmid is then cut with EcoRV and KpnI and the large vector fragment is gel-purified. The EcoRV/KpnI fragment of AcMNPV EcoRI-I fragment containing the wild-type polyhedrin promoter (SEQ ID NO: 6) and N-terminus is gel-purified and inserted into the vector fragment (EcoRV/KpnI) of pSPLSXIVVI+CAT to yield pLSXIVVI+CAT which contains the CAT gene under LSXIV promoter control and the intact polyhedrin gene under polyhedrin promoter control.

The viral vectors derived from these plasmids (vSPLSXIVVI+CAT and vLSXIVV+CAT) express equivalent or slightly higher levels of CAT than viruses expressing CAT under wild-type polyhedrin promoter control. An additional advantage of virus vectors derived from pLSXIVVI+CAT is that they produce polyhedrin at high levels.

Example VIII

Construction of pLSXIV3VI+ and pLSXIV2 transplacement plasmids (FIG. 13 and 14) is described. Plasmid pLSXIVVI+CAT is digested with BglII and EcoRI; the sticky ends removed with mung bean nuclease. The DNA is then cut with SacI and the large fragment is gel-purified and ligated to a multicloning site (MCS#3) having EcoRV and SacI termini to form pLSXIV3VI+lacking the CAT gene. This plasmid is then digested with EcoRV and KpnI. The large fragment is isolated and the EcoRV/KpnI fragment of pEVmodXIV is inserted into the large fragment resulting in pLSXIV2 which has two back-to-back LSXIV promoters, each with its own MCS. The pLSXIV3-VI+plasmid allows superior levels of foreign gene expression using the powerful LSXIV promoter (SEQ ID NO: 5) as well as polyhedrin gene expression. The pLSXIV2 plasmid allows superior expression of two foreign genes, each under LSXIV promoter control.

Example IX

Transplacement plasmid phc39 (FIG. 15) is constructed with the CAT reporter gene under the control of the vp39 promoter (SEQ ID NO: 6). Expression of CAT from vhc39 shows approximately 8 fold higher levels of CAT expression at 12 hrs post-infection than vhcwt, the vector carrying CAT under wild-type promoter control. The CAT gene of phc39 can be replaced with a heterologous gene of interest. Earlier expression during the infection process may allow more efficient post-translational modification of the heterologous protein product.

Example X

Transplacement plasmids are constructed to allow the simultaneous transplacement of two foreign genes into the virus vector and allow the recombinant viruses to simultaneously and abundantly express both foreign genes. The transplacement plasmid pSynwtVI- (FIG. 4) is one example of such a dual gene transplacement plasmid. This plasmid is constructed by digesting pSynVI- with SmaI and KpnI and inserting the pEV55 EcoRV/KpnI fragment containing the wild-type polyhedrin promoter and MCS#1. This plasmid thus contains two different multicloning sites, each downstream from back-to-back Syn and wild-type polyhedrin promoters.

Example XI

Figure 14:
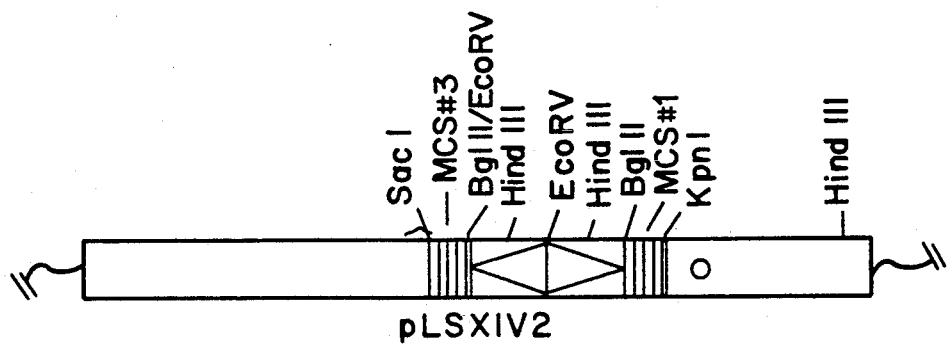
FIG. 14 is a schematic representation of the plasmid pLSXIV2.

Another example which allows even higher levels of the second gene is pLSXIV2 (FIG. 14). This plasmid provides back-to-back LSXIV promoters, each with a multicloning site (MCS#1 and #2) containing useful restriction sites for inserting two different foreign genes, each under the control of an LSXIV promoter. The efficacy of back-to-back promoters is tested using vLSXIVVI+CAT, a recombinant virus carrying the pLSXIVVI+CAT construct in which the LSXIV promoter drives CAT expression back-to-back with the polyhedrin promoter, which in turn drives polyhedrin gene expression. CAT expression by the vLSXIVVI+CAT vector was equivalent to or slightly higher than that observed with phcwt alone which expresses only CAT.

Example XII

Figure 16:
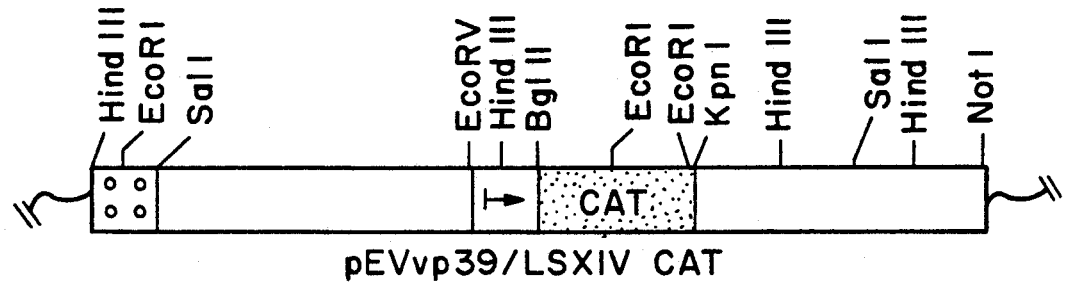
FIG. 16 is a schematic representation of the plasmid pEVvp39/LSXIV CAT.
Figure 17:
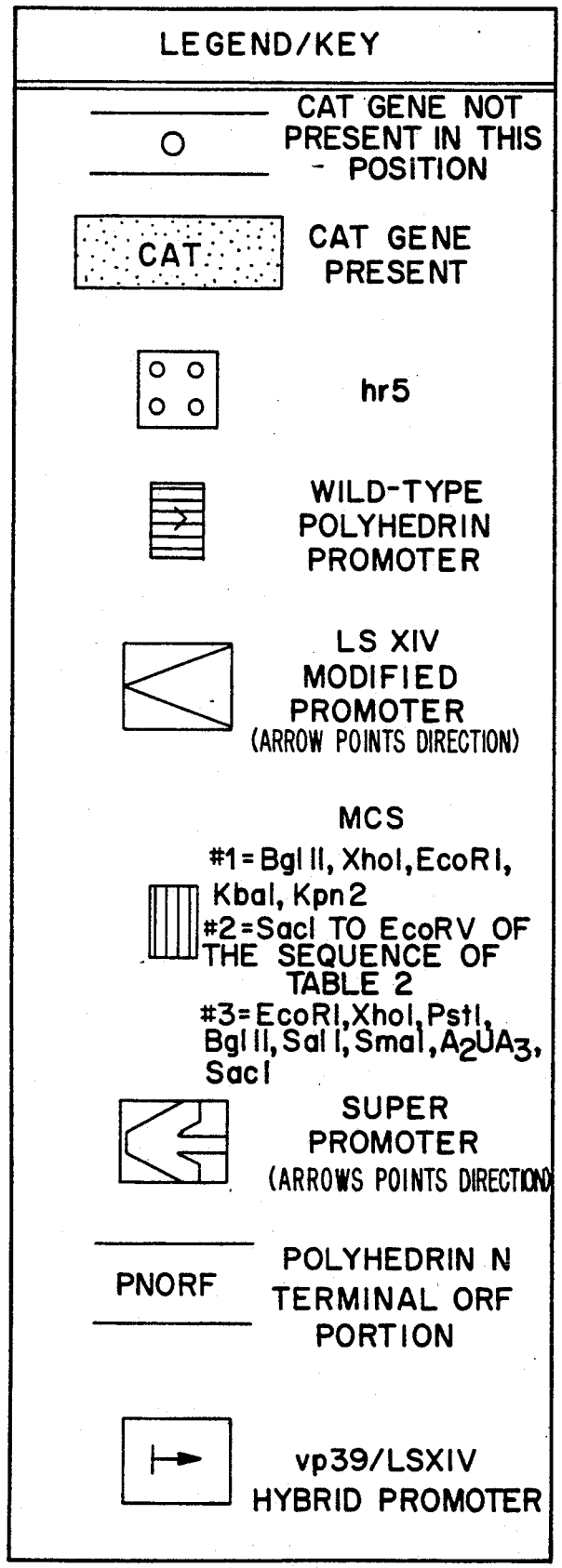
FIG. 17 is the legend for interpreting the plasmid schematics.

Construction of vp39/polyhedrin promoter fusions is described. HindIII linkers are inserted into the 462 bp promoter of vp39. The DNA sequence of vp39 is shown in Table 3 (SEQ ID NO: 8) (see Rankin et al. (1988) supra, for general linker scan approach). The HindIII linkers serve to allow interface with the HindIII sites of the linker-scan-modified promoters to generate late/very late combination promoters. Combination promoters are constructed which contain the OCT-A and OCT-B regions of vp39 (e.g., from −65 to approximately −350) fused to the +1 to approximately −60 of the polyhedrin promoter of the LSXIV promoter (SEQ ID NO: 5) of Rankin et al. (1988) supra. To do this, a plasmid is selected (e.g., pvp39-65) containing a HindIII linker at an appropriate site (e.g., −65). The HindIII to BglII fragment is replaced with the HindIII to BolII fragment of phcLSXIV. The entire BolII to EcoRV fragment containing the combination vp39/LSXIV promoter, can then be transferred to pEV55 to construct a transplacement plasmid, pEVvp39/LSXIVCAT (FIG. 16) with the combination promoter controlling CAT expression.

Example XIII

Construction of the transplacement plasmid pEVvp39/LSXIV (FIG. 16) is achieved in accordance with the method described in Example XII above. The sequence of the hybrid vp39/LSXIV promoter is shown in SEQ ID NO: 9 and Table 4. The sequence at the junction of the vp39/LSXIV combination promoter is marked by "1-10 CCAAGCTTG" which indicates a HindIII site at the junction (CCAAGCTTG) and approximately 1 to 10 nucleotides (N1-10) of the vp39 at the junction.

It should be understood, of course, that the foregoing relates only to preferred embodiments of the present invention and that numerous modifications or alterations may be made therein without departing from the spirit and the scope of the invention as set forth in the appended claims.

TABLE 1

DNA sequence for model synthetic baculovirus promoter of pSynVI (SEQ ID NO: 6)

G + C rich upstream "activator" region

| KpnI site | SmaI site | Hind III linker | | First capsid promoter start point |
|---|---|---|---|---|
| 5' GTACCT | CCCGGG | CCAAGCTTGG | CG | TTATTGAATAAGA |
| c a t g g a | g g g c c c | g g t t c g a a c c | g c | a a t a a c t t a t t c t |

| A + T rich region downstream of ATAAG | | Converged or conserved sequence of capsid + p10 promoter | Converged or conserved sequence of p10 + polyhedrin promoters |
|---|---|---|---|
| T's flanked by A's | A stretch preceded by y | | |
| ATTTA | AAAA | TCAATCA | TTTGTA |
| t a a a t | t t t t | a g t t a g t | a a a c a t |

| Converged or conserved sequence of p10 + 6.9K promoters | Polyhedrin + p10 reiterated sequence | Backward A₂UA₃ polyadenylation sequence | p10 + 6.9K and capsid sequence preceeding AT | EcoRV Site |
|---|---|---|---|---|
| TACTGTAAATTACA | TACTGTTTTATTT | | AACAAT | AGA 3' |
| a t g a c a t t t a a t g t | a t g a c a a a a t a a a | | t t g t t a | t c t 5' |

TABLE 2

DNA sequence including the sequence of multicloning site #2 (MCS #2) (SEQ ID NO: 7)

```
5' GAT                                          * * * * *
GT CCC GGG CC AAGCTT GGCG TTATTGAATAAGA ATTTA AAAA TCAATCA TTTGTA
   EcoRV/SmaI   HindIII              └──→

TACTGTAAATTACA TACTGTTTTATTT AACAATA {GATATC GAATTC CTGCAG CCGGG
                                      EcoRV   EcoRI  PstI
```

TABLE 2-continued

DNA sequence including the sequence of multicloning site #2 (MCS #2) (SEQ ID NO: 7)

| GGATCC | ACTAGT | TCTAGA | GCGGCCGC | CA | CCGCGG | TG | GAGCTC | CA} | ATC...3' |
|--------|--------|--------|----------|----|--------|----|--------|-----|----------|
| BamHI | SpeI | XbaI | NotI | | SacII | | SacI | | AcMNPV → |

TABLE 3 vp39 (capsid) promoter sequence in phc39 SEQ ID NO: 8

EcoRV
↓

G ATA TCT TGT TCG CCA TCG TGG AAT CAA ATA GAT CAA TGT CAC TTT TCG AAA AAT ATA CAT 62

GTT CAA ATT TGA TTT CAA TTT TAT CGT GTT GGT AAA CGT ACA CTT TAA TTA TTT TAC TCA 112

*
                         →
AGT TGT GCG AAA GAG TCT TGT AAG GCA GTT TGA TTT CTT TGC TTT CTC TCC ACA CCA ACG 182

GCA CCA ACG CGT TGG TAT CTT TAG GCC AAT AAA CAA ATT TTT TGT GTT TGG AAT TAG TCT 242

⌐ Oct B ⌐
TTT TCA CGC TTG ATA TTA TGT TAT TGC AAG CGC TCT GAA TAG GTA TAC GAG TGC GAA AGC 302

⌐ Oct A ⌐ **** →
CGT TTT CGT CGT ACA AAT CGA AAT ATT GTT TGC CAG CGA ATA ATT AGG AAC AAT ATA AGA 362

* 
                        →
ATT TAA AAT TTT ATA CAA CAA ATC TTG GCT AAA ATT TAT TGA ATA AGA GAT TTC TTT CTC 422

AAT CAC AAA ATC GCC GTA GTC CAT ATT TAT AAC GGC AAC AAT ATG
                                                     CAGATCT
                                                            ↑
                                                            BglII

TABLE 4 vp39/LSXIV hybrid promoter sequence SEQ ID NO: 9

EcoRV
↓

G ATA TCG CCA TCG TGG AAT CAA ATA GAT CAA TGT CAC TTT TCG AAA AAT ATA CAT

GTT CAA ATT TGA TTT CAA TTT TAT CGT GTT GGT AAA CGT ACA CTT TAA TTA TTT TAC TCA

*
AGT TGT GCG AAA GAG TCT TGT AAG GCA GTT TGA TTT CTT TGC TTT CTC TCC ACA CCA ACG

GCA CCA ACG CGT TGG TAT CTT TAG GCC AAT AAA CAA ATT TTT TGT GTT TGG AAT TAG TCT

⌐ Oct B ⌐
TTT TCA CGC TTG ATA TTA TGT TAT TGC AAG CGC TCT GAA TAG GTA TAC GAG TGC GAA AGC

⌐ Oct A ⌐ * 
CGT TTT CGT CGT ACA AAT CGA AAT ATT GTT TGC CAG CGA ATA ATT AGG AAC AAT ATA AGA

ATT TAA AAT TTT (N1-10ccaagcttg) CGC AAA TAA ATA AGT ATT TTA CTG TTT TCG TAA CAG TTT TGT AAT AAA AAA ACC TAT AAA TAG ATC
                             BglII

TABLE 5
Nucleotide sequences of the wild-type and mutant polyhedrin promoter/leader region.

A

EcoRV

GATATCATGGAGATAATTAAAATGATAACCATCTCGCAAATAA
−92

```
                                        ATAAGTATTTTACTGTTTTCGTAACAGTTTTGTAATAAAAAAACCTATAAAT
                                        −50                                                 −1
```

AGATCTCGACGAGATTTTCAGGAGCTAAGGAAGCTAAAATGGA
BglII

```
                                        GAAAAAAATCACTGGATATACCACCGTTGATATATCCCAATGGCATCGT...
```
XhoI/SalI

B

```
             −90       −80       −70       −60
phcwt       GATATCATGGAGATAATTAAAATGATAACCATCTCGCAAATAA
                                    −50       −40       −30       −20       −10       −1
                                    ATAAGTATTTTACTGTTTTCGTAACAGTTTTGTAATAAAAAAACCTATAAATAG phcLSXVI    GATATCATGGAGccaagcttggTGATAACCATCTCGCAAATAA
                                    ATAAGTATTTTACTGTTTTCGTAACAGTTTTGTAATAAAAAAACCTATAAATAG phcLSXVII   GATATCATGGAGATAATTAAAAccaagcttggCTCGCAAATAA
                                    ATAAGTATTTTACTGTTTTCGTAACAGTTTTGTAATAAAAAAACCTATAAATAG phcLSXIV    GATATCATGGAGATAATTAAAATGccaagcttggCGCAAATAA
                                    ATAAGTATTTTACTGTTTTCGTAACAGTTTTGTAATAAAAAAACCTATAAATAG
```

(A) The nucleotide sequence of phcwt from the EcoRV site (−92) through the N-terminal region of the cat gene is presented along with the positions of the BglII site at −1 and the fusion of the XhoI (from pEV55) and SalI (from cat cartridge) sites. The start codon ATG of cat is doubly underlined. The 8 nt constituting the major determinant for polyhedrin gene expression are underlined. An asterisk indicates the start point of transcription. This sequence is now identified as SEQ ID No 1.
(B) Nucleotide sequences of the wt and LS promoter/leader region. For the LS mutants, the linker replacement sequences are in lower-case letters. The asterisk at nt −50 indicates the start point of transcription. All nucleotides are numbered so that the last digit of the number corresponds to the given nucleotide.
phcwt, phcLSXVI, phcLSXVII and phcLSXIV are now identified as SEQ ID NO: 2, SEQ ID NO: 3, SEQ ID NO: 4 and SEQ ID NO: 5, respectively.

---

I claim:

1. A nuclear polyhedrosis virus vector for production of a gene product in a host cell capable of being infected by said virus vector, wherein the production of the gene product is under the regulatory control of a modified late or very later baculovirus promoter, which modified baculovirus promoter comprises a polyadenylation signal opposite in orientation to the direction of transcription directed by said modified promoter, and wherein said polyadenylation signal is placed 3' to the transcription start site of said modified promoter.

2. The nuclear polyhedrosis virus vector of claim 1 which is an *Autographa californica* virus vector.

3. A nuclear polyhedrosis virus vector for production of a gene product in a host cell capable of being infected by said virus vector, wherein the production of the gene product is under the regulatory control of a modified late or very later baculovirus promoter, which modified baculovirus promoter comprises two copies of a transcription start site, said transcription start site consisting essentially of one of the DNA sequences ATAAG or GTAAG, said copies oriented in the same direction and said copies of said transcription start site being separated by from 37 to 264 bp.

4. The nuclear polyhedrosis virus vector of claim 3 which is an *Autographa californica* virus vector.

5. A nuclear polyhedrosis virus vector for production of a gene product in a host cell capable of being infected by said virus vector, wherein the production of the gene product is under the regulatory control of a modified late or very later baculovirus promoter, which modified baculovirus promoter comprises conserved sequences present in untranslated leader regions of more than one abundantly expressed baculovirus later and/or very late promoter, said conserved sequences being ordered as in SEQ ID NO: 6.

6. The nuclear polyhedrosis virus vector of claim 5 which is an *Autographa california* virus vector.

7. A nuclear polyhedrosis virus vector for production of a gene product in a host cell capable of being infected by said virus vector, wherein the production of the gene product is under the regulatory control of a modified late or very late baculovirus promoter, which modified baculovirus promoter comprises a transcription activating sequence consisting essentially of about 10 bp of a DNA sequence having at least 60% G+C, said transcription activating sequence being placed about 10 to about 30 bp upstream of the transcription start site.

8. The nuclear polyhedrosis virus vector of claim 7 which is an *Autographa californica* virus vector.

9. The nuclear polyhedrosis virus vector of claim 8, wherein the modified baculovirus promoter is selected from the group of plasmids consisting of phcLSXIV, phcLSXVI, phcLSVIV2, pLSXIV3VI+ and pEV-modXIV.

10. A nuclear polyhedrosis virus vector for production of a gene product in a host cell capable of being infected by said virus vector, wherein the production of the gene product is under the regulatory control of a modified late or very late baculovirus promoter, which modified vaculovirus promoter consists essentially of the DNA sequence given in SEQ ID NO: 6.

11. The nuclear polyhedrosis virus vector of claim 10 which is an *Autographa californica* virus vector.

12. A modified nuclear polyhedrosis virus promoter comprising a copy of a synthetic baculovirus promoter is given in SEQ ID NO: 6 positioned in tandem with the modified baculovirus promoter of phcLSXIV as given in SEQ ID NO: 5, having the characteristics of the modified baculovirus promoter of pSPLSXIVVI+-CAT.

13. A method of preparing a nuclear polyhedrosis virus expression vector suitable for expression of a heterologous gene in a host cell capable of being infected by said virus vector, which method comprises the step of inserting into a nuclear polyhedrosis virus genome a modified late or very late baculovirus promoter selected from the group consisting of (a) such promoters comprising a polyadenylation signal opposite in orientation to the direction of transcription directed by said modified promoter, and wherein said polyadenylation is placed 3' to the transcription start site of said modified promoter; (b) such promoters comprising two copies of a transcription start site consisting essentially of one of the DNA sequences ATAAG and GTAAG, said copies separated by from 37 to 264 bp and said copies oriented in the same direction; (c) such promoters comprising conserved sequences present in untranslated leaders of more than one late and/or very late promoter, said conserved sequences being ordered as in SEQ ID NO: 6; (d) such promoters comprising a transcription activating sequence consisting essentially of 10 bp of a GC-rich sequence having a nucleotide sequence of at least 60% G+C placed about 10 to about 30 bp upstream of the transcription start site; (e) such promoters consisting essentially of the DNA sequence as given in SEQ ID NO: 6; (f) such promoters comprising a plurality of features recited in items (a) through (e), wherein said heterologous gene is under the control of said modified baculovirus promoter.

14. The method of claim 13 wherein said expression vector is formed by contacting in insect cells a transplacement plasmid with a nuclear polyhedrosis virus which replicates in said insect cells and selecting for recombinant viruses which express the gene product of said heterologous gene.

* * * * *